United States Patent [19]

Brownlee

[11] E

[45] Reissued

Patent Number: Re. 31,974

Date of Patent: Aug. 27, 1985

[54] CARTRIDGE TYPE SEPARATION COLUMN AND HOLDER ASSEMBLY FOR LIQUID CHROMATOGRAPHS

[75] Inventor: Robert Brownlee, Los Altos Hills, Calif.

[73] Assignee: Brownlee Labs, Inc., Santa Clara, Calif.

[21] Appl. No.: 392,896

[22] Filed: Jun. 28, 1982

Related U.S. Patent Documents

Reissue of:

[64] Patent No.: 4,283,280
Issued: Aug. 11, 1981
Appl. No.: 116,466
Filed: Jan. 29, 1980

U.S. Applications:

[63] Continuation of Ser. No. 936,400, Aug. 24, 1978, abandoned.

[51] Int. Cl.[3] ..... B01D 15/08

[52] U.S. Cl. ..... 210/198.2; 55/386

[58] Field of Search ..... 210/656, 198.2; 55/386

[56] References Cited

U.S. PATENT DOCUMENTS

| | | | |
|---|---|---|---|
| 3,440,864 | 4/1969 | Blume | 210/198.2 X |
| 3,771,659 | 11/1973 | Fraser | 210/198.2 |
| 3,791,522 | 2/1974 | Eisenbeiss et al. | 210/198.2 |
| 3,855,130 | 12/1974 | Randau et al. | 210/198.2 |
| 3,904,527 | 9/1975 | Wilhelmson et al. | 55/386 X |
| 3,978,575 | 9/1976 | Berea et al. | 210/198.2 |
| 3,981,801 | 9/1976 | Knox | 210/198.2 |
| 4,026,803 | 5/1977 | Abrahams et al. | 210/198.2 |
| 4,070,284 | 1/1978 | Fudita et al. | 210/198.2 |
| 4,083,702 | 4/1978 | Hartigan et al. | 53/386 X |
| 4,084,718 | 4/1978 | Wadsworth | 210/198.2 X |
| 4,093,550 | 6/1978 | Stahl et al. | 210/198.2 |
| 4,162,977 | 7/1979 | Guillemin et al. | 210/198.2 |
| 4,168,235 | 9/1979 | Guillemin et al. | 210/198.2 |

*Primary Examiner*—John Adee
*Attorney, Agent, or Firm*—Robert B. Block

[57] ABSTRACT

Plastic seal plugs insert into each end of an elution column tube and are provided with flat gasket portions extending laterally to cover each tube end, a spring loaded hand-tightenable nut drives an end fitting from each end of a column holder extending alomst the length of the column to put the gasket portions and the tube in compression and create a seal between the end fitting, tube, at interposed gasket, the latter being entirely contained against cold flow or deformation by a close fitting recess in the end fitting which entirely captures the plastic gasket and tube end.

25 Claims, 5 Drawing Figures

CARTRIDGE TYPE SEPARATION COLUMN AND HOLDER ASSEMBLY FOR LIQUID CHROMATOGRAPHS

Matter enclosed in heavy brackets [ ] appears in the original patent but forms no part of this reissue specification; matter printed in italics indicates the additions made by reissue.

This is a continuation of application Ser. No. 936,400, filed Aug. 24, 1978 now abandoned.

TECHNICAL FIELD OF THE INVENTION

This invention relates to liquid chromatography and particularly to a cartridge type separation or elution column and holder assembly including end fittings and interconnections for interchangeably and replaceably coupling the column to an associated liquid chromatograph solely by hand-tightening of holder end caps and without tools.

BACKGROUND AND PRIOR ART

Heretofore it has been common to seal an end fitting into engagement with an elution column by mechanisms which require the use of tools such as wrenches and the like in order to make up and unmake the sealing arrangement. A conventional seal of this type is the compression fitting seal such as manufactured by Crawford Fitting Company of Cleveland, Ohio and sold under the trademark "Swagelok" or a similar seal made by Parker-Hannifin of Cleveland, Ohio. These compression fittings are quite reliable and rely on a metal to metal seal using a cone shaped ferrule which is driven into a cone shaped machined recess in an end fitting by an external nut threaded into or about the end fitting. In this way the ferrule is driven into the cone shaped recess which squeezes it into radial compression against the interposed tube to obtain a good metal-to-metal seal. While these fittings can be taken apart and reassembled satisfactorily, they require the use of wrenches and can be overtightened or insufficiently tightened depending upon the skill of the operator. It is very difficult to assess whether or not and when this type of seal has been made up to the proper amount.

Another type of seal utilizes a plastic cone shaped seal which is also arranged in a cone type configuration. However, the seal itself depends upon deformation of the plastic which may be of the polytetrafluoroethylene (Teflon) type. Such seals can be made up once but they are not reliable when disassembled and attempts are made to reseal using the same parts. Additionally, they require wrenches or other tools to make and break them. Unfortunately, polytetrafluoroethylene has a tendency to cold flow and such seals tend to lose their integrity over a period of time whether or not they are unmade.

As a last example, certain types of column end fitting seals in liquid chromatography utilize a metal-to-metal gasket which is interposed between the end fitting and the column sealing faces. While this provides a reliable seal the first time it is made, it cannot be unmade and reset many times without replacing the gasket. This type of seal also requires wrench type tools to make and unmake the same.

From the foregoing it can be seen that the existing seals each suffer from certain disadvantages, principally in the ability to be resealed and to be assembled and disassembled easily without the need for wrenches or other special tools. It will be appreciated that most columns of this type are relatively unsupported and that the difficulty of making and breaking seals arises in part from the necessity for the operator to have considerable physical dexterity in handling the apparatus which may be unsupported except by the attached semi-flexible capillary inlet and outlet tubing.

Furthermore, the aforementioned seals which operate utilizing cone shaped ferrules or other cone shaped seals to radially compress either the seal or deform the tube wall, operate at an angle to the liquid force which they are attempting to seal. As such, they are inherently mechanically inefficient since they operate at sealing force angles not aligned with the direction of pressure of the liquid being sealed, and do not lend themselves to possible operation by simple finger tightening of parts.

In addition to the foregoing the several components of the seals as described above comprise a plurality of parts which have to be assembled together in a particular order, certain of the parts being so small that they are readily misplaced. Because of this and the uncertainty of leakage on reconnection it has often been found necessary to replace the seal as a standard precautionary measure.

There is therefore a need for a new and improved elution column seal and holder assembly for use in liquid chromatographs.

OBJECTS OF THE INVENTION

It is a general object of the present invention to provide a new and improved cartridge elution column seal and holder assembly for liquid chromatrographs which will overcome the above limitations and disadvantages.

A further object of the invention is to provide an elution column seal and holder assembly of the above character which can be hand-tightened by strong or weak persons to the design sealing force which is reliable upon repeated disassembly and remaking and which achieves its rated pressure without deforming the sealing member.

A further object of the invention is to provide an elution column seal and holder assembly of the above character utilizing an inert plastic seal which is prevented from cold flow and in which deformation thereof is not essential to obtaining the sealing function.

A further object of the invention is to provide an elution column seal and holder assembly of the above character which requires no tools to make up or unmake and which is designed so that the force applied to the seal and used to make up the same operates exactly at 180° from the liquid pressure which is being contained by the seal so that the mechanical advantage does not rely on cone shaped seals which are deformed at an angle to that force.

A further object of the invention is to provide an elution column, seal, and holder assembly in which the seal itself further incorporates a filter in a single assembly, the filter being a removable part captured within a plug portion of the seal structure, the latter also serving to slip into close fitting engagement within each end of the elution column in such a way that the elution column, filter, and seal (and plug) become a replaceable cartridge, seal (and plug) and filter becoming a replaceable subassembly. Thus, the elution column seal is readily providable as a separate unit, interchangeable with other like columns of the same physical size and structure but having different packing or other characteristics. In this way the column and seal assembly form a unitary structure of those parts which are most frequently found necessary to replace.

A further object of the invention is to provide an elution column, seal, and holder assembly of the above character in which all the component parts including seals and the like are contained and attached to solid structural components so that there are no loose free seals or parts beyond the holder, the elution column, and the end fittings, the latter being substantially permanently attached to the pair of feed fittings connected to the associated liquid chromatograph by the inlet and outlet tubing. The abbreviation LC is used in the present specification and claims interchangeably with the full expressions liquid chromatograph(y).

SUMMARY OF THE INVENTION

In general the present invention employs a replaceable cartridge type separation or elution column and seal which consists of an elongate hollow metal tube having an end seal plug assembly adapted to accommodate a filter within a recess of the plug, the latter interfitting into and closing each end of the tube. A seal plug assembly is made of an inert plastic and is provided with a laterally extending portion forming a seal integrally formed with the plug, the seal overlapping the end of each end of the tube to prevent a transverse extending flat annular seal covering at each end. A pair of end fittings having a precisely matching recess therein overlap each end of the column and seal for receiving the same. Knurled cap nuts adapted for being hand-tightened engage each end of an elongate holder (of slightly less length than the column cartridge assembly) and through which the column is disposed, the cap nuts bearing upon the end fittings through spring washers of the Bellville type. The cap nuts engage open threads at each end of the holder so that tightening of the nuts is sufficient to put the holder in tension and to load the spring washers to create a compression seal of the plastic between the ends of the tube and the bottom of the recess in the end fittings. The load applied by deformation of the spring washers is adequate to reliably maintain a compression seal on the plastic gaskets which are totally confined laterally by the close-fitting dimensioning of the recess in each end fitting.

These and other objects and features of the invention will become apparent from the following description when taken in conjunction with the accompanying claims and the appended drawings of which:

DETAILED DESCRIPTION OF THE PREFERRED EMBODIMENT

In general, the present invention consists of a type LC column 6 together with the end plugs closing each end to form a cartridge; an end fitting and assembly 7; and a cartridge holder 8 and retaining cap nut 9 for interconnecting the same into well sealed and operative relation to each other. Generically these several parts are termed and comprise the LC column and holder assembly of the present invention. As given herein the LC column and holder assembly is completely symmetrical and its inlet and outlet parts are identical and interchangeable and that the LC column is reversable. Accordingly, the description herein will be given in the singular with reference to one end of the assembly but it should be understood that both ends are included.

Figure 1:
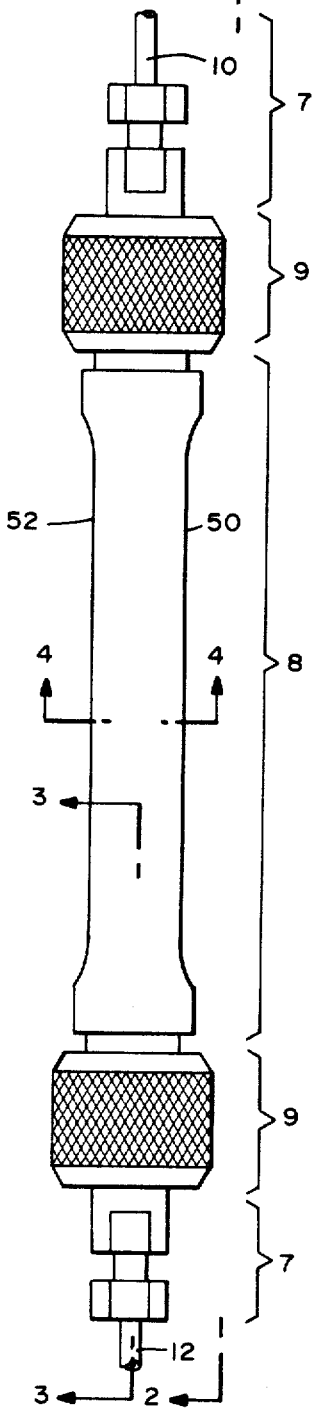
FIG. 1 is an elevational plan view of the liquid chromatograph column holder as constructed in accordance with the present invention.
Figure 2:
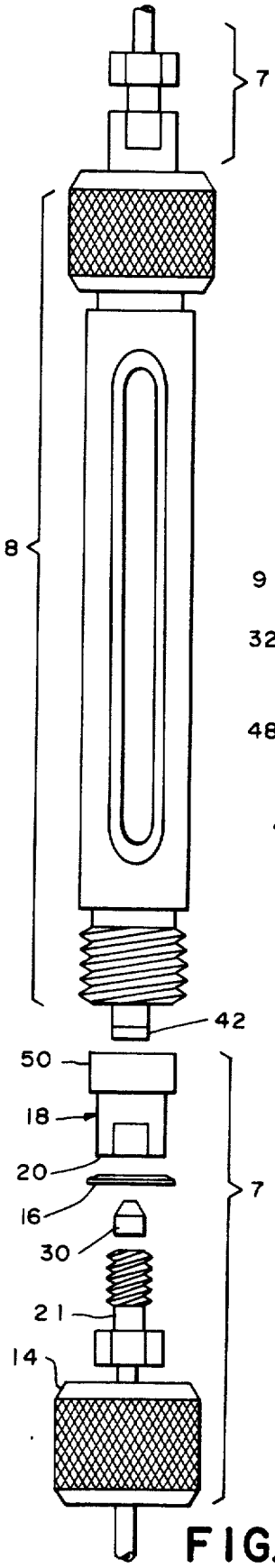
FIG. 2 is a plan view of the present invention of the liquid chromatograph column holder of FIG. 1 taken along the lines 2—2 of FIG. 1 but with one end thereof shown in exploded view, the other end being identical.
Figure 5:
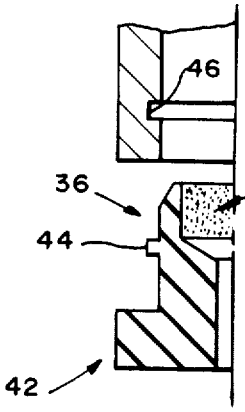
FIG. 5 is an exploded view of the cartridge tube and seal plug of the invention of FIG. 1.
Figure 3:
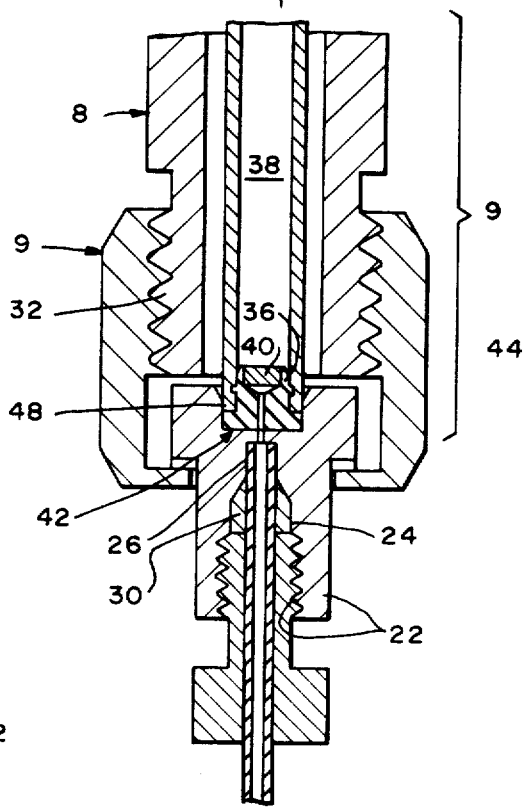
FIG. 3 is a cross-sectional view of the holder and column of FIG. 1 taken along the lines 3—3 thereof.
Figure 4:
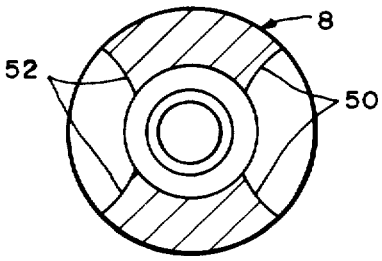
FIG. 4 is a cross-sectional view of the column and holder of FIG. 1 taken along the lines 4—4 thereof.

Referring particularly to the exploded portion of FIG. 2 and to FIG. 3, the inlet and outlet tubing 10, 12 from an LC pump (not shown) and the remainder of the liquid chromatograph passes freely through cap nuts 14 and spring washers 16 into a capillary engaging portion of a respective end fitting 18 which consists of an outwardly facing internally threaded projection 20 engaged by an externally threaded compression drive nut 21. These serve as part of means provided at each end of the column and holder assembly of the present invention for sealably engaging a semi-flexible tubing which interconnects the assembly to an associated liquid chromatograph. Since this connection will not need to be unmade, it is preferably the type which may remain relatively permanently installed. A variety of such connections are known, an example of which is illustrated in the drawings and is available under the trademark "Swagelok" as manufactured by Crawford Fitting Company of Cleveland, Ohio. Its remaining elements include a threaded section 22 followed by a conical section 24 tapering down to a capillary receiving recess 26, the latter being dimensioned to establish a close fitting relation with the end of the capillary. The tapered section is adapted to receive and cooperate with a conical compression ferrule 30. When tightened to specification the compression nut 21 provides a high pessure seal by radial compression of the ferrule 30 against the tubing 10, 12.

The inward column facing end of each cap nut 9 has a recess opening 32 which is internally threaded and adapted to engage the cartridge holder 8. The other end of the end cap is closed except for a central passage through which a capillary and capillary receiving projection 20 of an end fitting is permitted to freely pass. These parts are shown assembled in FIG. 3.

Referring now particularly to FIG. 3, the column is closed at each end with an end plug 34 as shown in detail in cross-section. The end plug is designed to serve three functions. The first is as a plug by providing a portion 36 to terminate the end of the column and to retain packing 38 therein and the second is as a carrier for an internally mounted filter unit 40. Thirdly, it provides a laterally extending portion 42 which overlaps the end of the column tube to form a gasket or seal member 42 which is the same diameter as the tube. The plug portion is about the same diameter as the inner diameter of the tube and extends internally therein in close fitting relation. Preferably, it is provided with a radially extending circumferential projection or rim 14 which interfits within a mating groove 46 machined at a depth to permit engagement by the projection when the plug is fully inserted. In this way the end plug is biased to remain in position during apparatus disassembly notwithstanding the close fitting relationship between the seal plug and the end fitting since the captured projection in the groove of the tube requires more force to unmake than the close sliding fit created between the seal and the end fitting 7. The filter can be of any suitable type such as a fine screen or sintered stainless steel frit and slidably inserted within a recess on the inner side of the plug. While the filter can be independently replaceable, it is usually more convenient to maintain a supply of seal plugs with filters installed so that the latter becomes a disposable and replaceable sub-assembly.

As shown, the end fitting is provided at its inner extreme with a recess 48 which is the same dimension as the column tube and seal portion 42 of the plug. The assembled cartridge is captured within the recess end fitting in a very close fitting relationship, contact being established between the outer, or endwise facing flat of the seal plug and the recess floor as well as between the seal and the side wall of the recess 48. In this way the laterally extending seal portions of the seal plug form a gasket like structure totally bounded at the outer extreme by the lower and/or floor of the recess and at its lateral sides by the side walls of the recess. The plug can be made of any suitable inert plastic, for example, and is preferably made out of polytetrafluoroethylene (PTFE). However, since PTFE is only machinable it may be desired to make the plug out of other similar materials which can be molded or extruded, such as polytetrafluoropropylene. The Bellville compression spring 16 is interposed between a laterally enlarged portion 50 of the end fitting surrounding the seal plug and tube receiving recess therein so that when assembled the compression spring is engaged between the end cap and cartridge ends to establish the magnitude of the sealing force of engagement between the end fitting and the seal of the cartridge assembly.

The end cap has certain physical dimensions which have been found to be particularly appropriate for use in the present application. Specifically, it is cut from $\frac{3}{4}$ diameter stock so that its nominal outer dimension is that size. The minimum outer dimension that would be suitable for handtightening operation is believed to be about $\frac{1}{2}$ inch or greater and the range is preferably of the order of $\frac{5}{8}$ to an inch. The inner threads of the end cap are 9/16 inch in diameter with 18 threads per inch as are the outer threads of the elongate tube holder. The spring washer compression force for flattening is approximately 130 pounds within about 0.009 inch travel. It can be readily shown that this combination or approximately this combination produces an assembly which may be hand-tightened to its designed specification by a person of relatively low strength and at the same time cannot be overtightened by a person of above average strength. Accordingly, the seal produced thereby is capable of achieving the design sealing specification without danger of being mishandled by operating personnel using a Bellville washer which required displacement of 9/1000 of an inch to achieve design compression of 130 pounds. The assembled unit was found to reliably achieve a reproducable seal of 500 psi which is adequate in the application for which this assembly was devised. In tests the seal achieved sealing forces of the order of 5,000 psi for a limited time and it is believed that reliable intermediate values could be obtained by redesign of the mechanical advantage and forces utilized.

The following additional specifications may be noted to derive a complete understanding of the cartridge assembly of the present invention and its implementation. The column tube constructed of 316 stainless steel LiChroma ID, $\frac{1}{4}$ inch in diameter, infernal diameter of the tube 0.180, external diameter of plug portion of seal plug 0.173, diameter of rim projection on seal plug 0.180, depth of filter element and associated recess 0.060 inches, depth of overlap seal at other end of seal plug 0.050 inches, diameter 0.250 inches. Cartridge assembly recess diameter 0.255 inches, depth 0.06 inches. The holder 8 and cap nuts 9 are aluminum.

As mentioned, the cartridge column, holder and associated parts are identical at each end as are all of the parts so that the device can be reversably assembled for reasons to be explained. In addition, the holder is somewhat shorter than the overall length of column including seal plugs so that compression force can be delivered by the end caps without interference which would be caused by engaging the ends of the holder itself.

A pair of finger slots are provided on opposite sides and along the length of the holder and serve the purposes of providing a finger gripping access to the column within the holder for removal of the same without disengaging both end caps and additionally provide a viewing window for reading the packing contents of the column which is in current use in the apparatus. The slots are conveniently provided by a tangential grinding operation to a $\frac{1}{4}$ diameter radius using a $\frac{1}{2}$ inch diameter ball end mill.

Thus there has been provided an exceptionally useful cartridge type column system for liquid chromatographs which, while having modest pressure rating nevertheless possesses many advantages for rapid chemical analysis with liquid chromatographs. The device requires only 25 pounds of force to seal a 500 psi liquid pressure which is easily achieved with a hand-tightenable knurled end cap driving through a Bellville spring washer against the cross-sectional area of the Teflon seal plug. The dimensions given permit a relatively weak person to achieve this minimum sealing force and rated pressure seal but the assembly is not so overdesigned that a strong person can overtighten it and deform the seal. It is an essential feature of this invention that the seal is not appreciably deformed in use even though made of inert polytetrafluoroethylene which normally cold flows. Such cold flow is detrimental to the function and operation of seals of this type since once PTFE is deformed it possesses hysteresis and does not return to its original character. This is an important reliability factor over time and also prevents the unit from being reassembled with the same seal.

A second feature of the present invention is that the seal is completely contained within the recess of the end fitting so that any tendency for cold flow is prevented from continuing because of the close fitting design of the recess.

Thirdly, the force which is delivered to the seal works is exactly opposition or 180° from the mechanical force which develops it. This is in distinction to other plastic polytetrafluoroethylene seals which are deformed and usually rely on cone shaped arrangements which work at a vector angle to the sealing force and thus lose mechanical advantage. The use of a spring type washer located between the end fitting and end cap accommodates both differential expansion of the stainless steel and aluminum parts and a certain amount of cold flow while still maintaining a seal with finger-tight assembly. This avoids design problems of many other seals which are not spring loaded and which become unreliable with time and that they tend to leak. In connection with leakage, the finger recess and viewing slots provide the additional function of immediate detection of any leakage since the same is not captured within the tube but visibly appears.

Thus there has been provided a unique and versatile cartridge elution column and holder assembly for liquid chromatographs which provides numerous advantages over previous designs and which is particularly designed so that the principal disposable parts are confined in a unitary cartridge assembly which is conveniently and easily replaceable without tools. In connection with the latter it might additionally be pointed out that the reversability of the cartridge lends itself to operations wherein only a small amount of time is required to obtain the component being eluded from the liquid mixture being passed through the column. In such applications after this portion has been retrieved, the column is then easily reversed in the holder and cleared by application of a suitable solvent. The clearing time when operated in reverse is often substantially less than that required to clear the column in a forward direction. Additionally, the certainty of the column being cleaned is established since the components elude through the column over a time frame which is identical to that originally employed and all of the sample is released in a single interval, i.e. similar to running a movie backwards to the first frame. Many adaptations and modifications of the invention will occur to those skilled in the art to which it pertains. Accordingly, the invention is to be defined solely by the scope of the following claims when interpreted in the light of the foregoing specification.

What is claimed is:

1. In a liquid chromatograph (LC) system in which a liquid is delivered under pressure from a pump to an LC column, a replaceable column cartridge and holder assembly adapted for removal, shipment, and handling as a self-contained unit including an elongate cylindrical metal tube, a sorbant filling said tube, a pair of plastic seal plugs for closing the ends of said tube, each of said plugs being of T-shape in cross-section with a leg constructed to extend into a respective end of the tube and having a laterally extending end flange portion overlapping the tube at each end to its outer diameter, said tube, seal plugs and said sorbant together forming self-supporting replaceable LC cartridge, fittings for interconnecting the cartridge in the LC output line between the pump output and the LC detector system, each fitting having a cartridge receiving recess therein formed within the body of said fitting and so dimensioned as to receive the same in close fitting relation so that each recess extends at least over the flange portions of said plugs so that the latter totally confined within the recesses by their sidewalls and are axially confined between the cartridge tube and the floor of recess, means for supporting said cartridge and for yieldably urging the cartridge under pressure into sealing engagement between the fittings, the sealing surfaces comprising the floor of each recess, the tube ends, and the interposed seal plug flange, all of which are oriented in direct opposition to leakage forces, said means for urging the column into sealing engagement within said fittings including a holder having an effective length together with said fittings to extend somewhat less than the length of the column, and having threaded portions formed at each end thereof, cap nuts having an open end provided with an associated recess therein having threaded portions for engaging the threaded portions of each end of the holder, the other end of said nut being partially closed to form a cap having an aperture therethrough, said end fittings having a projection extending through the respective aperture and a body contained within said cap recess, and spring means interposed between at least one cap nut and associated end fitting for yieldably urging the latter into engagement with the interposed cartridge as the cap nuts are taken up against said spring means so that said cartridge is placed end to end compression by said holder, cap nuts, and interposed spring means.

2. A liquid chromatograph column assembly as in claim 1 wherein said seal portion laterally extends from and is integral with the plug and is in the shape of a flat disc like portion, and, further in which the floor of said recess and the end of said tube are flat so that the end cap brings sealing forces to bear upon the seal plug in exact opposition to the mechanical force developing the seal as the cap nuts are tightened.

3. A liquid chromatograph column assembly as in claim 1 in which the plug portion of said seal plug is provided with a recess therein facing into the column tube, and a filter disposed within said recess.

4. A liquid chromatograph column assembly as in claim 1 in which the plug portion is provided with an outwardly extending ridge and in which the tube is provided with a mating groove so that when the plug is fully inserted to bring the seal into engagement with the end of the tube the same is only removable with an excessive force to overcome the interfit between said groove and ridge.

5. An assembly as in claim 1 in which said spring washer is of the Bellville type and is disposed between said cap nut and said end fitting so that when assembled a preestablished compression force equal to the spring constant of the washer is reliably and repletably established in compression on the cartridge unit.

6. A column assembly as in claim 1 in which said end cap has a diameter of about $\frac{3}{4}$ inch and is provided with a manually engageable surface, and in which said end nut and holder threads are about 18 per inch whereby said unit is hand-tightenable.

7. A liquid chromatograph column tube assembly as in claim 1 further in which said plug is provided with an outwardly facing circumferential rim intermediate its ends and transverse to its elongate dimension, and in which said tube is provided with an inwardly facing mating groove adjacent the end thereof for capturing the projection of the plug therein to reliably retain the same.

8. The system as in claim 1 wherein said plastic seal is selected from the group of polytetrafluoroethylene or polytetrafluoropropylene.

9. The system as in claim 1 wherein said spring means comprise Belleville washers interposed between each cap nut and the respective end fitting.

10. The system as in claim 1 further including a filter element, and in which said end plug is provided with a column facing recess for receiving and supporting said filter element.

*11. An improved column cartridge for use in a liquid chromatograph having a pump and connected to a column input line for delivering a sample and eluent under pres-*

*sure to an LC column and a column output line connected from the column to a detector for analyzing the column output, said cartridge comprising a circularly cylindrical solid tube having a bore therethrough, a chromatograph sorbent disposed in said bore, filter and seal means arranged across the opening of the bore at each end of the tube and mounted with the tube and sorbent as a self-contained unit to permit the same to be independently handled, said cartridge having no mounting structure associated therewith normally used to apply any force between any part of the cartridge and any external member, a pair of end fittings, each having one end connected to one of said input/output lines and the other end connected and arranged for mating contact with a respective of said column cartridge, a seal interposed between each said end fitting and said column cartridge, said cartridge seal and each end fitting being constructed and arranged to mate and to center together so as to establish a high pressure sealing configuration when placed in axial compression, means for contacting the outer ends of said end fittings for placing the same under axially directed inward force pushing said fittings against the ends of said cartridge, said cartridge being constructed to receive the compression force created by said end fittings and contacting means.*

*12. A chromatograph column comprising a cartridge adapted to be connected to a chromatograph by input and output lines and removable from the system and reusable and resealable therein, said cartridge including a circularly cylindrical solid tube having a bore therethrough, a chromatograph sorbent disposed in said bore, means including a filter arranged across the opening of the bore at each end of the tube and mounted with the tube and sorbent as a unit to permit the same to be independently shipped, sold and used, said cartridge having no mounting structure associated therewith normally used to apply any force between any part of the cartridge and an external member, a pair of end fittings, each having one end connected to one of said input/output lines and the other end connected and arranged for mating contact with said column cartridge, a seal interposed between each said end fitting and said cartridge, said seal and each end fitting being constructed and arranged to mate and to center together so as to establish a high pressure sealing configuration when placed in axial compression, means for contacting the outer ends of said end fittings for placing the same under axially directed inward force pushing said fittings against the ends of said cartridge.*

*13. The liquid chromatograph as in claim 12 in which said means for contacting said end fittings comprises an elongate holder tube threaded at at least one end, cap nut means for engaging said holder tube threated end and for capturing said end fitting therein.*

*14. The liquid chromatograph as in claim 13 further including means disposed between said end cap means and said end fitting forming a bearing between the same as the cap nut is taken up.*

*15. An LC system in which a liquid is delivered under pressure to an elution column comprising, a replaceable cartridge carrying no structure for mounting the same and including an elongate cylindrical tube formed of a single piece of stock, said tube having an exterior surface which is circularly cylindrical from end to end, said tube having a bore therein extending from end to end, a sorbent filling said bore, filter means inserted in the bore at each end and affixed interiorily to said tube for closing the ends to form said cartridge into a self-contained structure capable of being handled and stored as a separate part independently of mounting structure, said tube, filter means, and sorbent being constructed and arranged as a symmetrical structure so that said cartridge is reversible, a pair of end fittings for connecting the cartridge into the LC output line between the LC pump and the LC detector system, each fitting having a cartridge receiving recess formed of a portion of the body of the fitting and so dimensioned as to mate with portions of the tube at the end thereof, one of said tube and said fittings having a recess therein in which the other member is confined axially and laterally and supported therein, sealing means interposed between cartridge and the respective end fittings and means for yieldably urging the end fittings into compression against the ends of the seals and cartridge, and means for urging the column into sealing engagement with the fittings including a holder having an effective length together with the fittings to extend somewhat less than the length of the column and having threaded portions of each end of the holder, the other end of the nut being partly closed to form a cap having an aperature therethrough, said end fittings having a projection extending through the respective aperature and the body contained within a capped recess, and means interposed between the capnut and the associated end fitting for yieldably urging the latter into engagement with the innerposed cartridge as the capnuts are taken up against the same whereby the cartridge is placed end-to-end compression by said holder, capnuts, and interposed means.*

*16. In an LC system in which a liquid is delivered under pressure to an elution column, a replaceable cartridge characterized by carrying no structure for mounting the same, a holder and end fitting assembly means for carrying all the mounting hardware for engagement of the cartridge for high pressure operation, said cartridge comprising an elongate cylindrical tube formed of a single piece of stock, said tube having an exterior surface which is circularly cylindrical from end to end, said tube having a bore therein extending from end to end, a sorbent filling said bore, filter means including a resilient seal inserted in the bore at each end and affixed interiorly to said tube for closing the ends; said tube, filter means, and sorbent being constructed and arranged as a symmetrical structure so that said cartridge is reversible, a sealing surface provided at each end of said tube and facing toward each end fitting, said end fitting having a sealing surface constructed to lie in sealing relation to said tube surfaces, seal means interposed between said sealing tube and end fitting surfaces, and having portions exposed for contact by the LC system end fittings, said seal and filter means being formed as an integral unitary structure.*

*17. A cartridge system for a liquid chromatograph in which a liquid is delivered under pressure to an elution column comprising a replaceable cartridge carrying no structure for mounting the same and including an elongate cylindrical tube formed of a single piece of stock, said tube having an exterior surface which is circularly cylindrical from end to end, said tube having a bore therein extending from end to end, a sorbent filling said bore, filter means inserted in the bore at each end and affixed interiorily to said tube for closing the ends to form said cartridge into a self-contained structure capable of being handled and stored as a separate part independently of mounting structure; said tube, filter means, and sorbent being constructed and arranged as a symmetrical structure so that said cartridge is reversible, a pair of end fittings for connecting the cartridge into the LC output line between the LC pump and the LC detector system, each fitting having a cartridge receiving recess formed of a portion of the body of the fitting and so dimensioned as to mate and seal with por-*

*tions of the cartridge tube at the end thereof as the end fitting is placed in axially directed pressure against the ends of the cartridge, one of said tube and each said fitting having a recess therein in which the other member is confined axially and laterally and supported therein, sealing means interposed between each end of the cartridge and the respective end fitting, and means for yieldably urging the end fittings into axially directed compression against the ends of the sealing means of the cartridge to place the same under in axially directed pressure sufficient to obtain a direct, seal by axial compression between the ends of the cartridge and the axially directed portion of the recesses with the end fittings.*

*18. The system as in claim 17 in which said means for urging the end fittings is constructed and arranged for hand tightening such that fully effective sealing forces are obtained.*

*19. The system as in claim 18 in which said hand tightenable means comprises a holder in the form of a tube threaded at each end and extending coaxially of and around the cartridge, and capnuts threaded for engagement onto the holder and having portions thereof for engaging said end fittings for urging them against the ends of the cartridge.*

*20. The liquid chromatograph system as in claim 17 in which said means for urging the column into sealing engagement within the fittings includes a holder having an effective length together with the fittings to extend somewhat less than the length of the column and having threaded portions formed at each end thereof, capnuts having an open end having threaded portions for engaging the threaded portions of each end of the holder, the other end of the capnut being partly closed to form a cap portion having an aperture therethrough, said end fittings having a projection extending through the respective aperature and the body which is contained within the capnut.*

*21. A cartridge column system for a liquid chromatograph in which a liquid is delivered under pressure to an elution column comprising an end fitting assembly including means for carrying all the mounting hardware for end-to-end axial compression of the cartridge for high pressure sealing and operation, a replaceable cartridge characterized by an absence of structure for gripping or mounting the same, said cartridge comprising an elongate cylindrical tube formed of a single piece of stock strong enough to withstand end-to-end axial compression applied by the mounting hardware and transmitted end-to-end through the tube, said tube having an exterior surface which is circularly cylindrical from end to end, said tube having a bore therein extending from end to end, a sorbent filling said bore, filter means including a resilient seal inserted in the bore at each end and affixed interiorily to said tube for closing the ends; said tube, filter means, and sorbent being constructed and arranged as a symmetrical structure so that said cartridge is reversible, said seal having portions exposed for contact by the LC system end fittings.*

*22. The cartridge column system as in claim 21 in which said filter means includes plug means dimensioned to fit into and mounted to be retained in the respective end of the tube and a frit filter disposed in said plug means.*

*23. The cartridge column system as in claim 21 further including a seal integrally formed as part of said means and includes a plastic member having a surface adapted to be interposed between said end fitting and portions of said tube and constructed and arranged for sealing engagement therebetween as the urging means is taken up.*

*24. The cartridge column system as in claim 21 in which said seal means is formed in the shape of a "T" cross-section the arms of which extend laterally over the ends of the tube, the base of which contains said filter and forms a projection extending into the end of the tube for being retained therewith.*

*25. The cartridge column system as in claim 21 in which said tube is provided with a sealing surface facing toward each end fitting, and in which said end fitting is provided with a sealing surface constructed to lie in sealing relation to said tube end surface, and further including seal means interposed between said sealing tube and end fitting surfaces.*

* * * * *